(12) United States Patent
Takesako et al.

(10) Patent No.: US 6,333,305 B1
(45) Date of Patent: Dec. 25, 2001

(54) ANTIBIOTIC TKR2999, PROCESS FOR THE PREPARATION THEREOF AND MICROBE

(75) Inventors: Kazutoh Takesako; Naoyuki Awazu; Mitsuhiro Ueno; Yoshimi Onishi, all of Shiga; Ikunoshin Kato, Kyoto, all of (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

(21) Appl. No.: 09/582,025

(22) PCT Filed: Dec. 22, 1998

(86) PCT No.: PCT/JP98/05797

§ 371 Date: Aug. 2, 2000

§ 102(e) Date: Aug. 2, 2000

(87) PCT Pub. No.: WO99/32498

PCT Pub. Date: Jul. 1, 1999

(30) Foreign Application Priority Data

Dec. 22, 1997 (JP) .................................................. 9-365697

(51) Int. Cl.[7] .......................... A01N 37/18; A01K 38/00
(52) U.S. Cl. .................. 514/2; 435/254.1; 435/71.3; 514/183; 514/192; 514/200; 260/112; 260/112.5; 930/10
(58) Field of Search ................................ 514/2, 183, 192, 514/200; 260/112, 112.5; 930/10; 435/254.1, 71.3

(56) References Cited

FOREIGN PATENT DOCUMENTS

| 9-249680 | 9/1997 | (JP) . |
| WO 97/34012 | 9/1997 | (WO) . |
| WO 98/21196 | 5/1998 | (WO) . |
| WO 98/56755 | 12/1998 | (WO) . |

*Primary Examiner*—Christopher R. Tate
*Assistant Examiner*—Brett Ozga
(74) *Attorney, Agent, or Firm*—Sughrue Mion, PLLC

(57) ABSTRACT

The antibiotic TKR2999 having the physicochemical properties described below and its pharmacologically acceptable salt:

(1) FAB-MS m/z 971 [M+H]$^+$, (2) the molecular formula: $C_{44}H_{78}N_{10}O_{14}$, and high-resolution FAB-MS m/z 971.5776 [M+H]$^+$, (3) the ultraviolet absorption spectrum in methanol has an end absorption, (4) the infrared absorption spectrum by KBr method shows the major absorption wave numbers at 3320, 2920, 1680, 1540, 1210, 1140, 840, 800, and 720 cm$^{-1}$, (5) aspartic acid, threonine, serine, glycine, alanine, β-alanine, and ornithine are detected by the amino acid analysis using ninhydrin reaction, and (6) the solubility is that it is soluble in methanol, and practically insoluble in hexane, chloroform, and water.

3 Claims, 5 Drawing Sheets

ANTIBIOTIC TKR2999, PROCESS FOR THE PREPARATION THEREOF AND MICROBE

TECHNICAL FIELD

The present invention relates to the antibiotic TKR2999, which is useful as a therapeutic agent for fungal infection diseases, a method for its production, and microorganisms producing it.

BACKGROUND ART

Fungi are known to cause a variety of infectious diseases in man, animals, and plants. In man, for instance, they cause superficial mycosis affecting the skin, oral cavity, etc. and systemic mycosis affecting the viscera, brain, etc. They cause similar infections in pet and domestic animals as well. Furthermore, fungi inflict various hazardous effects on plants such as orchard trees and vegetables.

As the principal pathogenic fungi causing systemic mycosis in man, those of the genera Candida, Cryptococcus, and Aspergillus, among others, are known. As to superficial mycosis, Candida species affecting the skin, oral cavity, and vagina and trichophytons infecting the skin of the extremities are regarded as the major pathogenic fungi. Besides those fungi, many other fungi exist in the environment and are suspected to contaminate the animal and vegetable kingdoms.

As antimycotics of use for the prevention and treatment of such fungal infections and contaminations, only a very few are known. As therapeutic drugs for systemic mycosis in man and animals, for instance, amphotericin B, flucytosine, miconazole, and fluconazole can be mentioned. However, those compounds are not fully satisfactory in potency, toxic potential, or antifungal spectrum, thus being not impeccable as therapeutic drugs.

In view of the above-mentioned prior art, the present invention has for its object to provide a novel antibiotic which is of value as a therapeutic agent for fungal infections.

In the search for a novel antibiotic, the inventors of the present invention isolated a large number of microorganisms from the natural kingdom, isolated the antibiotics they produced, and scrutinized their biological properties. As a result, they discovered that the culture broth of a strain of microorganism of the Fungi Imperfecti contained an antibiotic having antifungal activity against pathogenic fungi inclusive of Candida albicans, C. kefyr, Cryptococcus neoformans, and Aspergillus fumigatus. Accordingly the inventors isolated this antibiotic and studied its physicochemical properties. As a result, they discovered that it was a novel substance having distinct physicochemical characteristics, which had been described in no literatures yet, and named it TKR2999. The present invention intends to provide the above antibiotic TKR2999 and a method of production thereof.

The present inventions are described in detail as follows.

DISCLOSURE OF THE INVENTION

The above antibiotic TKR2999 has the physicochemical properties of (1), (2), (3), (4), and (5) described below:

(1) the mass spectrum by FAB-MS method gives an ion peak of $[M+H]^+$ at m/z 971;

(2) the molecular formula is represented by $C_{44}H_{78}N_{10}O_{14}$, and its mass spectrum by high-resolution FAB-MS gives m/z 971.5776 as $[M+H]^+$;

(3) the ultraviolet absorption spectrum in methanol has an end absorption;

(4) the infrared absorption spectrum by KBr method shows the major absorption wave numbers at 3320, 2920, 1680, 1540, 1210, 1140, 840, 800, and 720 $cm^{-1}$;

(5) aspartic acid, threonine, serine, glycine, alanine, β-alanine, and ornithine are detected by the amino acid analysis using ninhydrin reaction; and (6) the solubility is that it is soluble in methanol, and practically insoluble in hexane, chloroform, and water.

The antibiotic TKR2999 mentioned above shows the $^1$H-NMR spectrum shown in FIG. 3 and the $^{13}$C-NMR spectrum shown in FIG. 4, and is characterized in the reversed-phase high-performance liquid chromatography, in which it is eluted at the position indicated in FIG. 5.

The above-mentioned antibiotic TKR2999 can be produced by growing a strain of microorganism belonging to the class Fungi Imperfecti and capable of producing said TKR2999 in a culture medium, and by isolating the substance from the culture broth of the above strain.

The strain of microorganism used in the present invention is not limited and can be used only provided it is capable of producing said TKR2999. An example of the strain that is used for production of the said compound is the fungi TKR2999 (hereinafter referred to as the TKR2999-strain) belonging to the class of Fungi Imperfecti.

The above-mentioned TKR2999-strain is a novel strain not heretofore described in a literature, and was isolated and characterized for the first time by the inventors of the present invention. The strain has the property to produce TKR2999 with advantage. The mycological characteristics of this TKR2999-strain are now described in detail as follows.

The colors of colonies of said TKR2999-strain on various media are shown in Table 1. The description of colors in the table is based on those prescribed in Japanese Industrial Standard (JIS) Z 8102 (1985). The results of observation on days 14 of culture at 25° C. after inoculation are shown.

TABLE 1

| Medium | Diameter of colony (mm) | Color of colony | Surface color of colony | Appearance of colony |
| --- | --- | --- | --- | --- |
| Malt extract agar | 29 | grayish yellow-red 5YR5/2 | sepia 10YR3/2 | velvety |
| Potato dextrose agar | 37 | dark gray N3 | little dark yellow 2.5Y3/2 | velvety |
| Sabouraud agar | 28 | dark yellowish gray 5Y4/1 | little dark yellow 2.5Y3/2 | velvety |
| YpSs agar | 26 | light yellowish gray 5YR7/1 | dark grayish blue-green 2.5BG3/2 | velvety |

The above TKR2999-strain grows slowly on malt extract agar, potato dextrose agar, and Sabouraud agar etc. The colony has velvety surface and rises in the center with dense hard mycelia. Conidia of the TKR2999-strain are unicellular, cylindrical with smooth surface, and the both edges are round. Their size is 3–8×1.5–2.5 μm. Conidia are formed well on the above medium, but the conidia formation style in view of the conidiophore is uncharacterized.

Among the mycological characters of the TKR2999-strain, its physiological characteristics are as follows.

Temperature range for growth: the temperature range for growth is 10 to 30° C. and the optimum range of temperature for growth is around 25° C.

The pH range for growth: the pH range for growth is pH 3 to 9 and the optimum range of pH for growth is pH 5.

The above mycological characters are compared with the descriptions of species of the class Fungi Imperfecti described in "A Manual of Soil Fungi" authored by Joseph C. Gilman (Constable and company Ltd.) (1959) etc. The species of the TKR2999-strain can not be identified because its conidia formation style is unidentified.

However, no report was available on a strain of microorganism having the ability to product TKR2999 among strains of the class Fungi Imperfecti. Therefore, the inventors of the present invention regarded it as a novel strain and named it Fungi strain TKR2999 of the Fungi Imperfecti. The strain was deposited under the Budapest Treaty with the National Institute of Bioscience and Human Technology (Address, 1-3, Higashi 1-chome, Tsukuba-shi, Tbaraki, Japan (Zip code 305-0046)) under the accession number of FERM BP-6524 (original date of deposit: Nov. 21, 1997; date of request for transfer to international deposit: Sep. 24, 1998).

The present invention can be carried into practice not only with the above-mentioned TKR2999-strain but also with any spontaneous or artificial mutant of the TKR2999-strain or any other strain of microorganism belonging to the class Fungi Imperfecti and capable of producing TKR2999.

In accordance with the present invention, TKR2999 is produced by cultivating a TKR2999-producing strain described above in a nutrient medium. Nutrients to be used for the medium include various carbon sources such as glucose, fructose, saccharose, starch, dextrin, glycerol, molasses, malt syrup, oils and fats, and organic acids.

Nutrients to be used for the medium include nitrogen sources, organic and inoragnic materials such as soybean meal, cotton seed meal, corn steep liquor, casein, peptone, yeast extract, meat extract, wheat germs, urea, amino acids, ammonium salts, etc. Salts as nutrients are various inorganic salts such as salts of sodium, potassium, calcium, magnesium, etc. and salts of phosphoric acid. Those materials can be used independently or in a suitable combination.

Where necessary, the nutrient medium may be supplemented with heavy metal salts such as iron salts, copper salts, zinc salts, cobalt salts, etc., vitamins such as biotin, vitamin B1, etc., and other organic and inorganic substances which would assist in growth of the microorganism and promote production of TKR2999.

In addition to the above components, an antifoamer and/or a surfactant, for example silicone oil, polyalkylene glycol ethers, etc., can be added to the nutrient medium.

In cultivating a strain of microorganism capable of producing TKR2999 in said nutrient medium, a variety of cultural methods which are generally used in the production of antibiotics by means of microorganisms can be employed. However, a liquid culture method, particularly a method by shake culture or submerged aerobic culture, is preferred.

The cultivation is preferably carried out at 15 to 25° C. The pH of the medium may range from pH 3 to 8 and is preferably around pH 5. Regarding the incubation time, generally a sufficient output of the substance can be expected by 6 to 15 days of culture.

By means of the above cultivation, TKR2999 is contained both intracellularly and extracellularly and accumulated in the culture broth. In the present invention, the TKR2999 accumulated in the culture broth can be recovered and isolated from the broth by utilizing its physicochemical characteristics and, where necessary, by further purification.

The above-mentioned recovery can be achieved by extracting the whole broth with a non-hydrophilic organic solvent such as ethyl acetate, butyl acetate, chloroform, butanol, methyl isobutyl ketone, or the like. As an alternative, it is possible to subject the broth to centrifugation or filtration to separate into the medium and cells and isolate the antibiotics from each of the medium and cells.

For separation of TKR2999 from the medium not only the above-mentioned extraction method using a non-hydrophilic organic solvent but also the method which comprises contacting the medium with an adsorbent to let TKR2999 adsorbed on the adsorbent and desorbing or eluting them with a solvent can be employed.

The adsorbent that can be used includes, for example, activated carbon, cellulose powder, and adsorbent resins. As the above-mentioned solvent, a variety of solvents can be selectively used according to the kind and properties of the adsorbent and either singly or in combination. Thus, an aqueous solution of one or more water-soluble organic solvents, such as aqueous acetone, aqueous alcohol, etc., can be employed. For separation of TKR2999 from the cells, the extraction technique using a hydrophilic organic solvent such as acetone can be employed.

In the present invention, the crude extract of TKR2999 obtained from the culture broth as described above can be subjected to a procedure for purification when necessary. The purification can be carried out by conventional methods for separation and purification of hydrophobic antibiotics. Examples of the methods are column chromatographies or high-performance liquid chromatographies, using a column packed with a stationary phase such as silica gel, activated alumina, activated charcoal, adsorbent resin, etc. The eluent that can be used for silica gel column chromatography includes chloroform, ethyl acetate, methanol, acetone, water, a mixture of thereof, etc.

The resin for high-performance liquid chromatography includes chemically-derivatized silica gel, such as silica gel derivatives having octadecyl, octyl, or phenyl groups, and polystyrenic porous polymer gels, while the mobile phase that can be used includes aqueous solutions of water-soluble organic solvents, such as aqueous methanol, aqueous acetonitrile, etc.

TKR2999 of the present invention can each be put to use as such or in the form of a pharmacologically acceptable salt in medicinal applications. There is no particular limitation on the type of pharmacologically acceptable salt. Thus, the salt includes salts of mineral acids such as hydrochloric acid, sulfuric acid, nitric acid, phosphoric acid, hydrofluoric acid, hydrobromic acid, etc., salts of organic acids such as formic acid, acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, camphorsulfonic acid, etc., and salts of alkali metals or alkaline earth metals, such as sodium, potassium, calcium, etc.

To administer TKR2999 or its pharmacologically acceptable salt, as a drug, they can be administered to animals inclusive of humans either as such or in the form of a pharmaceutical composition containing typically 0.1 to 99.5%, preferably 0.5 to 90% thereof in a pharmaceutically acceptable, non toxic and inert carrier.

The carrier mentioned above includes solid, semisolid or liquid diluents, fillers, other formulation auxiliaries, etc. and such carriers can be used alone or in combination.

The above-mentioned pharmaceutical composition is preferably administered in unit dosage forms and can be administered orally, parenterally, topically (e.g. transdermally) or rectally. Of course, those pharmaceutical compositions should be administered in dosage forms suited for the respective route of administration.

For administration of TKR2999, or its pharmacologically acceptable salt, as a drug, the dose as an antifungal agent is preferably selected with reference to patient factors such as age and body weight, route of administration, nature and severity of disease, etc. Usually in man, however, the daily dose of the active ingredient for an adult patient is 10 to 2000 mg. While a daily dose lower than the above range may be sufficient in some cases, a dose higher than the range may be required in other cases. When a high dose is used, the daily dosage is preferably administered in several divided doses.

The above oral administration can be made using solid, powdery, or liquid dosage forms such as bulc powders, powders, tablets, dragees, capsules, drops, subligual tablets, etc.

For the above parenteral administration, liquid unit dosage forms for subcutaneous, intramuscular, or intravenous administration, typically solutions and suspensions, can be employed. These preparations can be manufactured by suspending or dissolving a predetermined amount of TKR2999, or a pharmacologically acceptable salt thereof, in a nontoxic liquid carrier suitable for injection, such as an aqueous medium or an oily medium, and sterilizing the resulting suspension or solution.

The topical administration (e.g. transdermal administration) can be carried out using a variety of topical dosage forms such as liquids, creams, powders, pastes, gels, and ointments. These dosage forms can be manufactured by using a predetermined amount of TKR2999 or a pharmacologically acceptable salt thereof, in combination with one or more of the perfume, coloring agent, filler, surfactant, humectant, emollient, gelatinizer, carrier, preservative, stabilizer, etc., suitable for topical dosage formulations.

The rectal administration can be made using, for example, suppositories each mixing a predetermined amount of TKR2999, or its pharmacologically acceptable salt of the present invention, with a low-melting solid base such as higher esters, e.g. myristyl palmitate, polyethylene glycol, cacao butter, or a mixture of them.

BEST MODE OF CARRYING OUT THE INVENTION

Figure 1:
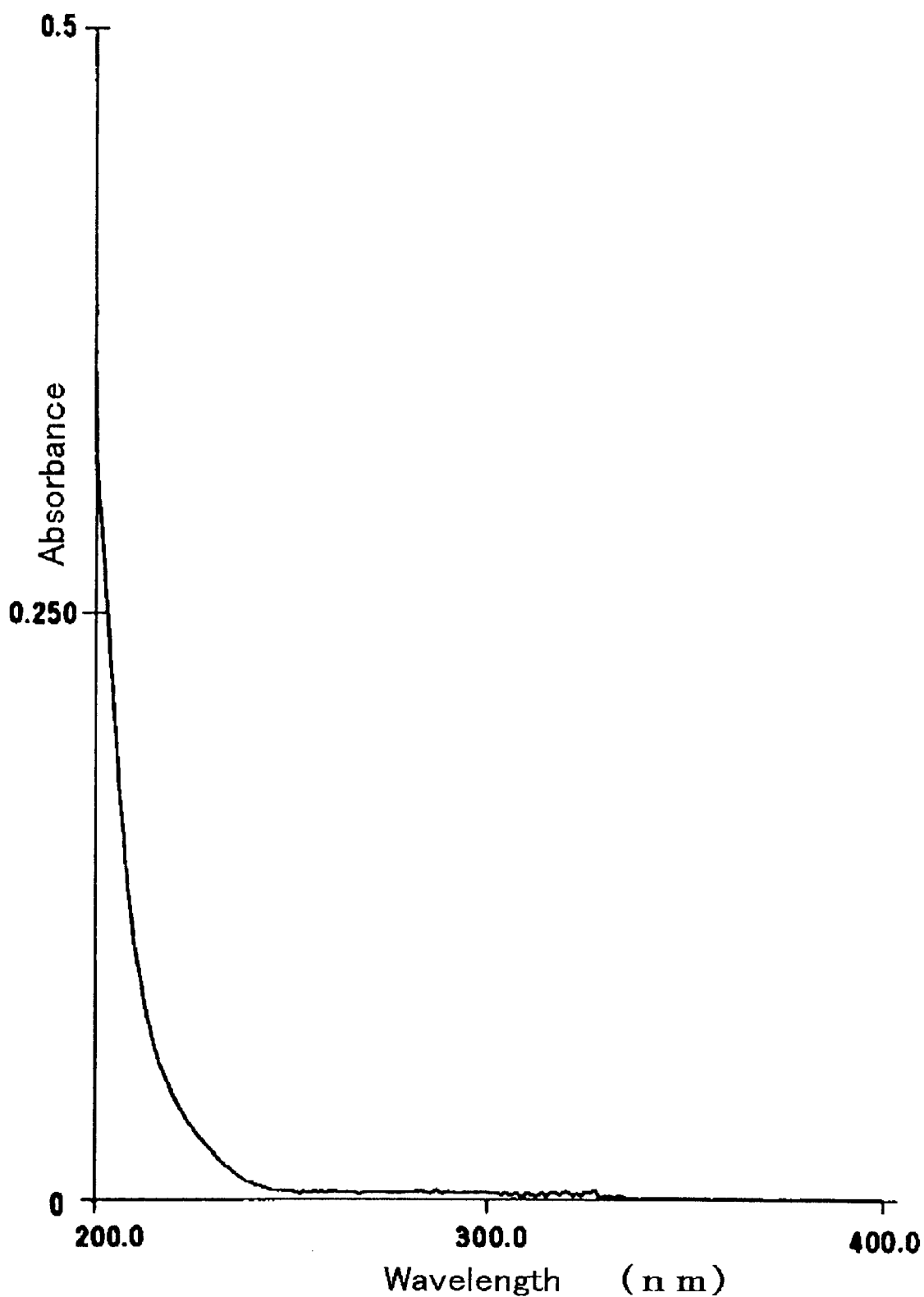
FIG. 1 is an ultraviolet absorption spectrum of the antibiotic TKR2999. The ordinate represents absorbance and the abscissa represents wavelength (nm).

A loopful of the TKR2999-strain (FERM BP-6524) from a slant culture was used to inoculate into a 500-ml Erlenmeyer flask containing 100 ml of liquid medium (Difco yeast nitrogen base 0.67% (w/v) and glucose 2.0% (w/v)) and incubated on a shaker at 25° C. for 10 days to prepare a seed culture. This seed culture, 1.0 ml, was transferred to each of 26 Erlenmeyer flasks of 500 ml capacity each containing 120 ml of the same liquid medium as above and incubated (under shaking at 220 rpm) at 25° C. for 12 days. The culture broth obtained was centrifuged and separated into the supernatant and the cells.

The cells obtained were mixed with 1 L of methanol and subjected to sufficient mixing for extraction. The extract was concentrated under reduced pressure. The residue was mixed with 300 ml each of water and butanol, and subjected to sufficient mixing to perform extraction with butanol. The extract was concentrated under reduced pressure to recover 362 mg of a residue. The residue was dissolved in 2 ml of methanol and subjected to high-performance liquid chromatography to provide an active fraction. The fraction was concentrated under reduced pressure to recover 1.2 mg of purified TKR2999 as white powder. The high-performance liquid chromatography was carried out under the following conditions.

Apparatus: LC-8A (Shimadzu)
Column: YMC pack C18 (2.0 cm×25 cm) (YMC)
Mobile phase: 60% (v/v) of acetonitrile/water containing 0.05% trifluoroacetic acid Physicochemical Properties Mass spectrometry was carried out by JMS-DX302 mass spectrometer (Jeol Ltd.). $^1$H-NMR spectrum (in deuterated dimethylsulfoxide with deuterated dimethylsulfoxide as reference) and $^{13}$C-NMR spectrum (in deuterated dimethylsulfoxide with deuterated dimethylsulfoxide as reference) were measured by JNM-A500 nuclear magnetic resonance spectrometer (Jeol Ltd.). Ultraviolet spectrophotometry (in methanol) was carried out by UV-250 self-recording spectrophotometer (Shimadzu), and infrared absorption spectrometry (KBr method) was by 270-30 infrared spectrophotometer (Hitachi). Physicochemical properties of the substance TKR2999 are desribed below.

(1) Mass Spectrometry and Determination of the Molecular Formula

The purified white powdery product available upon vacuum concentration of the active fraction in said high-performance liquid chromatography was found to be a substance with m/z 971 [M+H]$^+$ by measurement with FAB-MS. In addition, its high resolution FAB-MS was measured and an [M+H]$^+$ was observed at m/z 971.5776. This result gave the molecular formula of $C_{44}H_{78}N_{10}O_{14}$ (calculated, 971.5699) to TKR2999.

(2) Ultraviolet Absorption Spectrum

The UV absorption in methanol of the purified white powdery product available upon vacuum concentration of the active fraction in the high-performance liquid chromatography was found to be end absorption.

The UV absorption spectrum is shown in FIG. 1.

(3) Infrared Absorption Spectrum

The IR spectrophotometric characterization (KBr method) of the purified white powdery product available upon vacuum concentration of the active fraction in the high-performance liquid chromatography was as follows. IR (KBr) (cm$^{-1}$): 3320, 2920, 1680, 1540, 1210, 1140, 840, 800, 720.

Figure 2:
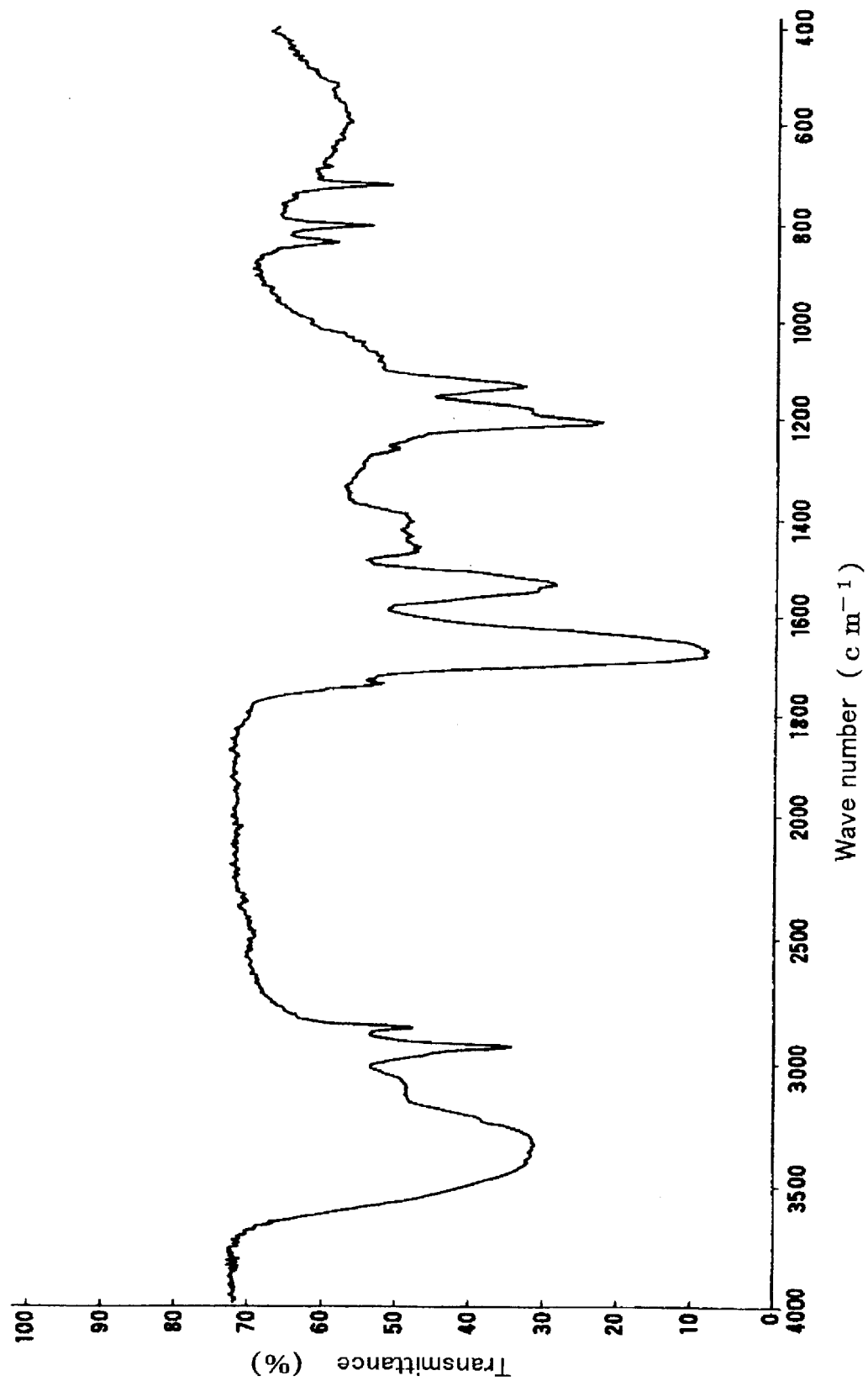
FIG. 2 is an infrared absorption spectrum of the antibiotic TKR2999. The ordinate represents transmittance (%) and the abscissa represents wave number (cm$^{-1}$).

The IR absorption spectrum is shown in FIG. 2.

(4) $^1$H-NMR and $^{13}$C-NMR Spectra

The purified white powdery product available upon vacuum concentration of the active fraction in the high-performance liquid chromatography was used to measure $^1$H NMR spectrum and $^{13}$C NMR spectrum.

Figure 3:
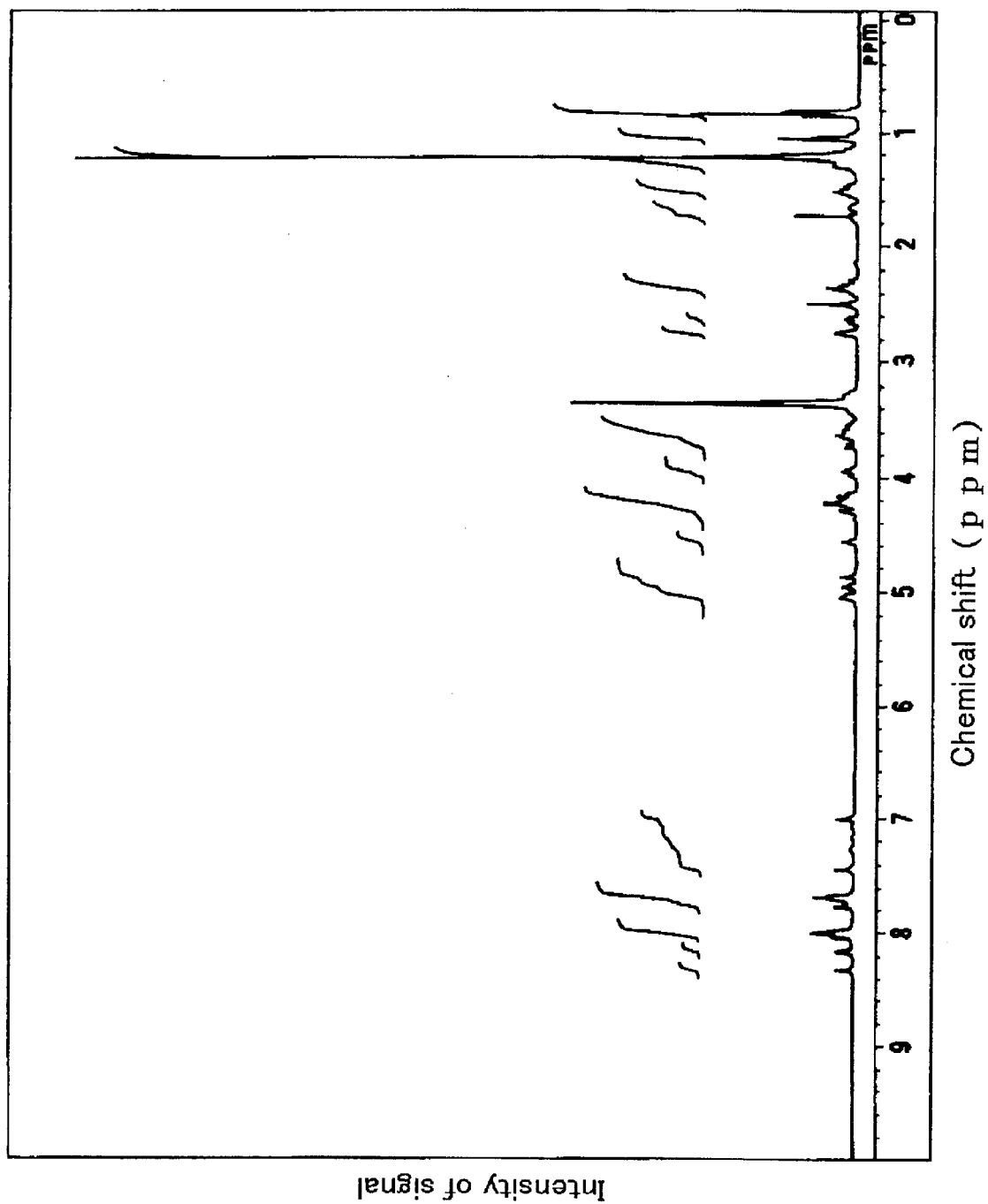
FIG. 3 is an $^1$H-NMR spectrum of the antibiotic TKR2999. The ordinate represents the intensity of signal and the abscissa represents chemical shift (ppm).
Figure 4:
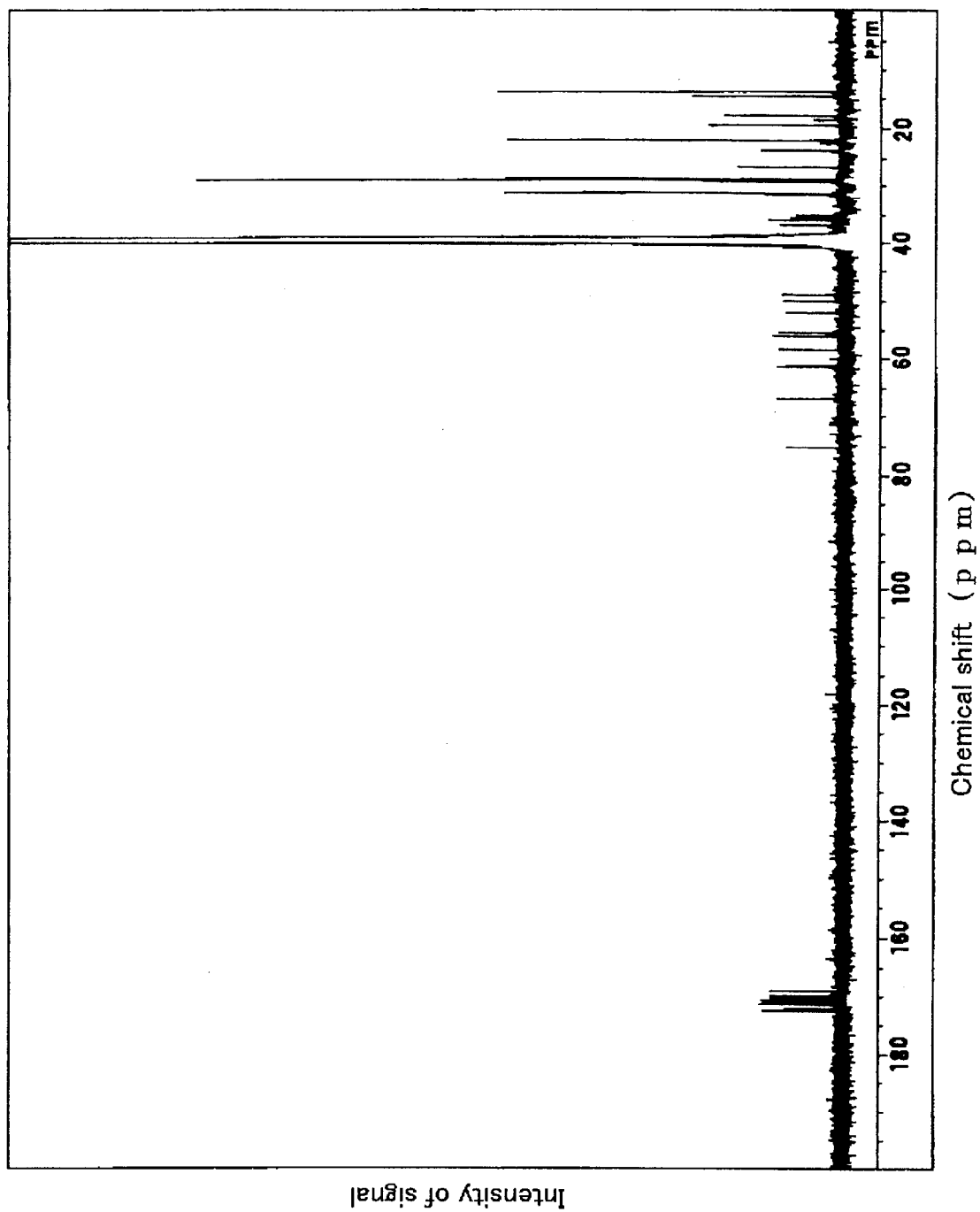
FIG. 4 is a $^{13}$C-NMR spectrum of the antibiotic TKR2999. The ordinate represents the intensity of signal and the abscissa represents chemical shift (ppm).

The $^1$H-NMR spectrum and $^{13}$C-NMR spectrum of this product are presented in FIG. 3 and FIG. 4, respectively.

(5) Amino Acid Analysis

The purified white powdery product available upon vacuum concentration of the active fraction in the high-performance liquid chromatography was hydrolysed in 6 N HCl at 110° C. for 24 hours. The decomposed product was analyzed by the amino acid analyzer, and aspartic acid, threonine, serine, glycine, and alanine were detected. Additionally β-alanine and ornithine were detected.

(6) As for the solubility of the this substance in various solvents, it was soluble in methanol, but practically insoluble in hexane, chloroform and water.

Based on the above analyses, the purified white powdery product available upon vacuum concentration of the active fraction in the high-performance liquid chromatography was identified to be TKR2999.

The above TKR2999 was analyzed by reversed-phase partition high-performance liquid chromatography (HPLC) using LC-10A high-performance liquid chromatography (Shimadzu). This HPLC analysis was carried out under the following conditions.

Column: CAPCELL PAK $C_{18}$ (6 mm×150 mm) (Shiseido)

Mobile phase: 50% (v/v) acetonitrile/water containing 0.05% trifluoroacetic acid Column temperature: 40° C.

Detection UV wavelength: 220 nm

Figure 5:
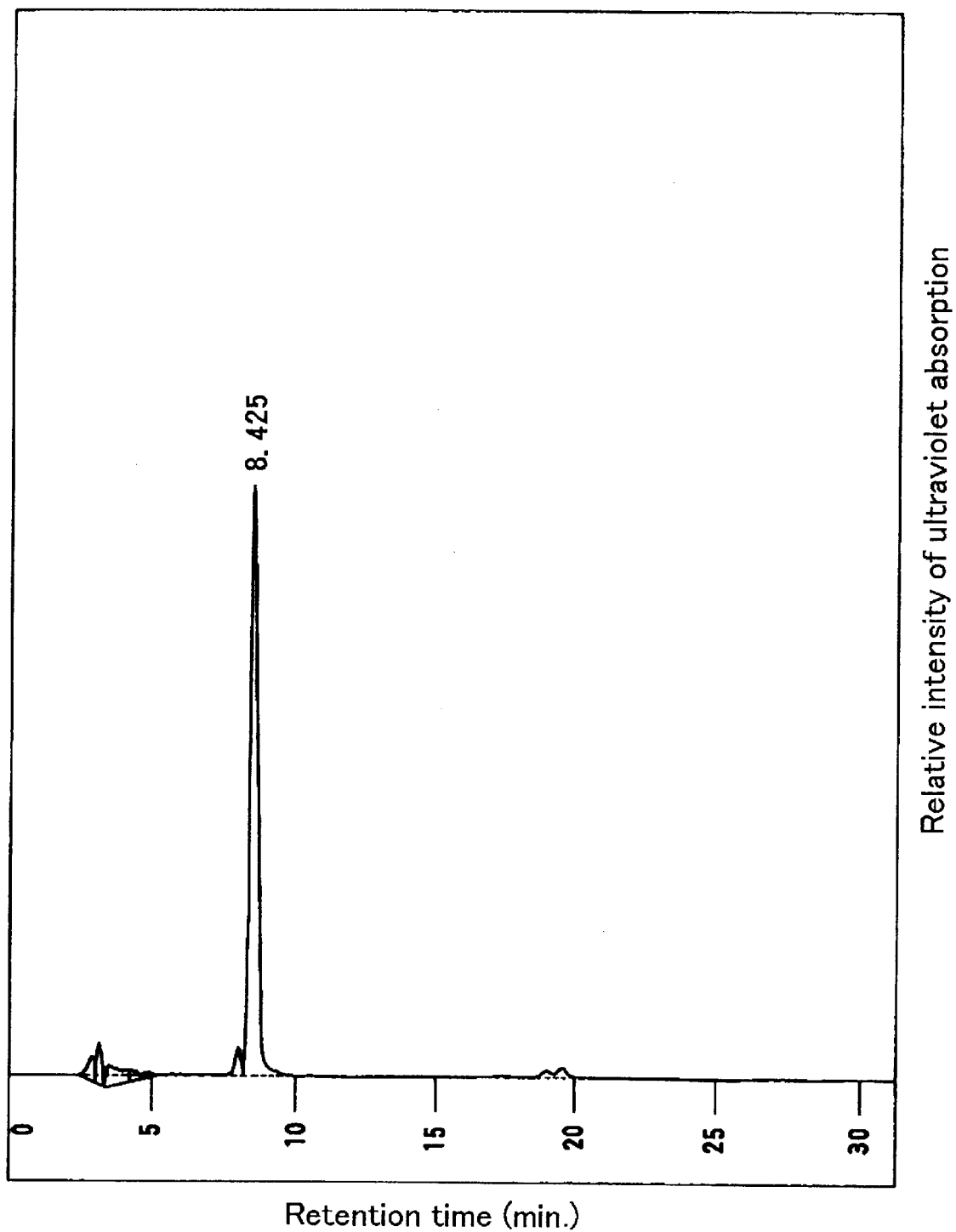
FIG. 5 shows an HPLC elution pattern of the antibiotic TKR2999. The abscissa represents the relative intensity of ultraviolet absorption and the ordinate represents retention time (min.).

As a result, the above TKR2999 was eluted at the position indicated in FIG. 5.

Biological Characteristics

The TKR2999 obtained was tested for the antimicrobial spectrum to various microorganisms. Using the liquid medium dilution method for the measurement, the concentration causing substantially complete inhibition of micorbial growth was determined as the minimal inhibitory concentration (µg/ml). The results are shown in Table 2. The minimal concentration causing partial inhibition of fungal growth was determined as the sub-inhibitory concentration (µg/ml) and are shown in parentheses in the table. In the table, YNBG stands for a medium comprising 0.67% of yeast nitrogen base (Difco) and 1.0% of glucose, and BHI does for a medium comprising 0.5% of brain heart infusion bouillon (Nissui).

TABLE 2

| Test strain | | Medium | Minimal inhibitory concentration (µg/ml) |
|---|---|---|---|
| Candida albicans | TIMM0136 | YNBG | 6.25 |
| Candida kefyr | TIMM0301 | YNBG | 12.5 (6.25) |
| Cryptococcus neoformans | TIMM0354 | YNBG | 6.25 (3.13) |
| Aspergillus fumigatus | TIMM1776 | BHI | 0.78 |

It is apparent from Table 2 that TKR2999, the antibiotic according to the present invention, is active against pathogenic fungi such as Candida albicans, Candida kefyr, Cryptococcus neoformans, Aspergillus fumigatus, etc. Intraperitoneal administration of the TKR2999 obtained above at a dose of 50 mg/kg to ICR mice caused no toxic signs.

INDUSTRIAL APPLICABILITY

The present invention provides the antibiotic TKR2999 which are of use in clinical medicine, for example in the therapy of fungal infectious diseases, and a method for production of the substance.

What is claimed is:

1. The antibiotic TKR2999 having the physicochemical properties of (1), (2), (3), (4), and (5) described below and its pharmacologically acceptable salt:

(1) the mass spectrum by FAB-MS method gives m/z 971 as $[M+H]^+$;

(2) the molecular formula is represented by $C_{44}H_{78}N_{10}O_{14}$, and its mass spectrum by high-resolution FAB-MS gives m/z 971.5776 as $[M+H]^+$;

(3) the ultraviolet absorption spectrum in methanol has an end absorption;

(4) the infrared absorption spectrum by KBr method shows the major absorption wave numbers at 3320, 2920, 1680, 1540, 1210, 1140, 840, 800, and 720 $cm^{-1}$;

(5) aspartic acid, threonine, serine, glycine, alanine, β-alanine, and ornithine are detected by the amino acid analysis using ninhydrin reaction; and (6) the solubility is that it is soluble in methanol, and practically insoluble in hexane, chloroform, and water.

2. A method for producing the antibiotic TKR2999, which comprises cultivating a strain of microorganism belonging to the class Fungi Imperfecti and capable of producing TKR2999 and harvesting the objective antibiotic from the resulting culture broth.

3. A biologically pure culture of a microorganism belonging to the class Fungi Imperfecti which produces the antibiotic TKR2999.

* * * * *